(12) United States Patent
Watakabe et al.

(10) Patent No.: US 8,977,031 B2
(45) Date of Patent: Mar. 10, 2015

(54) METHOD AND DEVICE FOR IDENTIFYING MULTIPOTENT STEM CELL COLONY, AND METHOD AND DEVICE FOR AUTOMATICALLY CULTURING MULTIPOTENT STEM CELLS

(75) Inventors: Keizo Watakabe, Kobe (JP); Takashi Sakurai, Kobe (JP); Osamu Ohji, Kako-gun (JP); Katsumi Nakashima, Kobe (JP)

(73) Assignee: Kawasaki Jukogyo Kabushiki Kaisha, Kobe-shi (JP)

( * ) Notice: Subject to any disclaimer, the term of this patent is extended or adjusted under 35 U.S.C. 154(b) by 155 days.

(21) Appl. No.: 13/805,767

(22) PCT Filed: Jun. 22, 2011

(86) PCT No.: PCT/JP2011/003574
§ 371 (c)(1),
(2), (4) Date: Jan. 28, 2013

(87) PCT Pub. No.: WO2011/161962
PCT Pub. Date: Dec. 29, 2011

(65) Prior Publication Data
US 2013/0130228 A1    May 23, 2013

(30) Foreign Application Priority Data

Jun. 25, 2010   (JP) .................................. 2010-145468

(51) Int. Cl.
*G06K 9/00* (2006.01)
*G06T 7/60* (2006.01)
*C12M 1/34* (2006.01)
(52) U.S. Cl.
CPC ...................................... *C12M 41/46* (2013.01)
USPC ......................................... 382/133; 382/203

(58) Field of Classification Search
None
See application file for complete search history.

(56) References Cited

U.S. PATENT DOCUMENTS

| 5,720,928 A | 2/1998 | Schwartz |
| 6,147,198 A | 11/2000 | Schwartz |

(Continued)

FOREIGN PATENT DOCUMENTS

| EP | 2 143 791 A1 | 1/2010 |
| EP | 2 487 249 A1 | 8/2012 |

(Continued)

OTHER PUBLICATIONS

Jan. 28, 2014 Extended European Search Report issued in European Patent Application No. 11797850.2.

(Continued)

*Primary Examiner* — Jon Chang
(74) *Attorney, Agent, or Firm* — Oliff PLC

(57) ABSTRACT

A method and device achieves identification on whether a colony on a cultivation container is differentiated or undifferentiated on an occasion of cultivation of multipotent stem cell, and a method and device achieves a rapid culture of undifferentiated multipotent stem cells. Undifferentiated colony containing only undifferentiated multipotent stem cells is identified from other types of colonies by means of the circularity C of the colony in an image-processed taken image of the inside of cultivation container of a multipotent stem cell. More specifically, when a first threshold of the circularity of the colony is C1, and a second predetermined threshold is C2 (C1<C2), a colony satisfying C2≤C is determined as the undifferentiated colony, a colony satisfying C1≤C<C2 is determined as an undefined colony, and a colony satisfying C<C1 is determined as the differentiated colony.

19 Claims, 8 Drawing Sheets

(56) References Cited

U.S. PATENT DOCUMENTS

| | | |
|---|---|---|
| 6,294,136 B1 | 9/2001 | Schwartz |
| 6,404,497 B1 | 6/2002 | Backman et al. |
| 6,509,158 B1 | 1/2003 | Schwartz |
| 6,587,792 B1 | 7/2003 | Thomas |
| 6,610,256 B2 | 8/2003 | Schwartz |
| 6,624,890 B2 | 9/2003 | Backman et al. |
| 7,008,792 B2 | 3/2006 | Lopez et al. |
| 7,049,074 B2 | 5/2006 | Schwartz |
| 7,049,093 B2 | 5/2006 | Tsuji et al. |
| 2002/0086344 A1 | 7/2002 | Tsuji et al. |
| 2002/0171831 A1 | 11/2002 | Backman et al. |
| 2003/0036067 A1 | 2/2003 | Schwartz |
| 2003/0124611 A1 | 7/2003 | Schwartz |
| 2003/0179916 A1 | 9/2003 | Magnuson et al. |
| 2004/0091906 A1 | 5/2004 | Thomas |
| 2005/0176152 A1 | 8/2005 | Lopez et al. |
| 2006/0039593 A1 | 2/2006 | Sammak et al. |
| 2007/0212778 A1* | 9/2007 | Bramke et al. ............... 435/326 |
| 2007/0274963 A1* | 11/2007 | Green et al. ............... 424/93.7 |
| 2009/0029462 A1 | 1/2009 | Beardsley et al. |
| 2010/0074507 A1* | 3/2010 | Klottrup et al. ............... 382/133 |
| 2011/0019897 A1* | 1/2011 | Takagi et al. ............... 382/133 |
| 2012/0315620 A1 | 12/2012 | Watakabe et al. |

FOREIGN PATENT DOCUMENTS

| | | | |
|---|---|---|---|
| JP | A-2002-223791 | | 8/2002 |
| JP | A-2002-535027 | | 10/2002 |
| JP | A-2003-527106 | | 9/2003 |
| JP | A-2006-042663 | | 2/2006 |
| JP | A-2007-024612 | | 2/2007 |
| JP | A-2007-522475 | | 8/2007 |
| JP | A-2009-022284 | | 2/2009 |
| JP | A-2009-044974 | | 3/2009 |
| JP | A-2009-077635 | | 4/2009 |
| JP | 2010104301 A | * | 5/2010 |
| WO | WO 96/31522 A1 | | 10/1996 |
| WO | WO 00/42912 A1 | | 7/2000 |
| WO | WO 01/42786 A2 | | 6/2001 |
| WO | WO 01/51007 A2 | | 7/2001 |
| WO | WO 2008/117813 A1 | | 10/2008 |
| WO | WO 2009/006422 A1 | | 1/2009 |
| WO | WO 2011/043077 A1 | | 4/2011 |

OTHER PUBLICATIONS

Translation of pp. 84-91 of Seiki Inoue et al., "C-gengo de Manabu Jissen Gazo Shori," 1999, pp. 1-8.

Katsumi Nakashima et al., "Development of the Automatic Cell Processing Machine for the Adherent Cell," Inflamm Regen, 2009, vol. 29, No. 2, pp. 131-134 (with English Abstract).

Seiki Inoue et al., "C-gengode Manabu Jissen Gazo Shori," 1999, pp. 84-91.

Nakashima et al., "Automation of Cell Culturing for Regeneration Medicine," Biotechnology, 2007, vol. 85, No. 10, pp. 432-434 (with English Translation).

Dec. 7, 2010 International Search Report issued in Application No. PCT/JP2010/006007 (with English Translation).

* cited by examiner

METHOD AND DEVICE FOR IDENTIFYING MULTIPOTENT STEM CELL COLONY, AND METHOD AND DEVICE FOR AUTOMATICALLY CULTURING MULTIPOTENT STEM CELLS

TECHNICAL FIELD

The present invention relates to a method and a device for identifying multipotent stem cell colony and a method and a device for automatically culturing multipotent stem cells, and more specifically relates to a method and a device for identifying undifferentiated colony containing only undifferentiated multipotent stem cells and other types of colonies, and a method and a device for automatically culturing multipotent stem cells employing such method and such device.

BACKGROUND ART

In recent years, multipotent stem cells such as embryonic stem cells (ES cells), induced pluripotent stem cells (iPS cells) and the like (in the present Descriptions, the "ES cell" and the "iPS cell" are generically referred to as "multipotent stem cell") have been artificially created, and is expected to provide extensive contributions to the fields of the regenerative medicines and the like. Since the multipotent stem cells have pluripotency, in which the multipotent stem cells are capable of being differentiated into various types of cells that constitute the living body, the use of iPS cells of a patient himself/herself allows regenerations of skins, cartilages, bones, vessels, nerves, organs and the like without causing a rejection.

Since the multipotent stem cells have the pluripotency as described above, some of the multipotent stem cells can start their differentiation on the way of the cultivation. It is not possible to restore the cells starting the differentiation in this way back to an undifferentiated state again, and therefore cells in such condition cannot be employed for forming targeted organs and body parts. Therefore, on the occasion of the subculture of the multipotent stem cells, it is critical to ascertain whether or not the colonies of the cultured stem cells are undifferentiated to eventually separate only the undifferentiated multipotent stem cells out.

Identifications of such undifferentiated multipotent stem cells can be achieved by conducting a staining of cells or an observation of fluorescence via employing, for example, "Cell Celector®" commercially available from "AVISO Corporation". However, in general, the staining process is often conducted after immobilizing cells, and besides, staining agents often exhibit toxic effect for cells, and therefore it is difficult carry out an observation of living cells. Further, even if a staining agent of lower toxicity is employed, such a staining agent is still somewhat toxic to cells, and thus an application thereof to the field of regenerative medicine is not appropriate.

SUMMARY OF INVENTION

Technical Problem

Additionally, upon conducting identification of undifferentiated multipotent stem cells, an attempt for acquiring a taken image of a cultivation container, processing the taken image, and using the processed image of the taken image to determine whether or not every colony is an undifferentiated colony, based on the luminance of the colony (Japanese Patent Application No. 2009-235306). However, when the undifferentiated colony is identified based on only the luminance of the colony, precise identification may not be made depending upon conditions. Additionally, since every one of the identifications should be individually carried out for all colonies, considerably longer time is required until the determination for the entire cultivation container is completed, causing problems of changing the states of cells in the cultivation container.

The present invention is made in order to solve these problems related to the above-described conventional technologies, and therefore, it is an object of the present invention to provide a method and device for achieving identification on whether a colony on a cultivation container is differentiated or is undifferentiated, on an occasion of a cultivation of multipotent stem cells, and to provide a method and a device for achieving a rapid culture of the undifferentiated multipotent stem cells.

Solution to Problem

The present invention is made based on a discovery, in which, on one hand, a shape of a colony created only with undifferentiated multipotent stem cells is closer to circular, and on the other hand, a shape of a colony containing differentiated multipotent stem cells is not circular. More specifically, a method for identifying a colony according to the present invention is a method for identifying a colony, in which an undifferentiated colony and an undefined colony are identified based on a taken image inside of an incubator of multipotent stem cells, wherein, when a predetermined first threshold of a circularity of the colony is C1 and a second threshold of the circularity of the colony is C2 (C1<C2), a circularity C of the colony is obtained by calculation, and a colony satisfying $C2 \leq C$ is determined as the undifferentiated colony containing only undifferentiated multipotent stem cells, and a colony satisfying $C1 \leq C < C2$ is determined as an undefined colony that is potentially the undifferentiated colony.

Here, in the Descriptions of the present invention, the term "multipotent stem cells" is defined as cells including "differentiated multipotent stem cells" and "undifferentiated multipotent stem cells", and the terms "differentiated multipotent stem cells" and "differentiation multipotent stem cells" are defined as multipotent stem cells starting their differentiation or cells that are differentiated from the multipotent stem cells. The circularity C is a value defined by $C=(4\pi S)/(L \times L)$. Here, S is an area of the colony, and L is a boundary length of the colony. Therefore, it can be understood that, when the shape of the colony is circular, the circularity C is C×1, and the circularity C decreases as the shape of colony is distorted, and the circularity C also decreases when an outer circumference of the colony is notched.

The above-described method for identifying a colony additionally includes a configuration, in which it is further determined that a colony satisfying $C<C1$ is the differentiated colony containing multipotent stem cells.

In addition, the above-described method for identifying a colony additionally includes the configuration, in which the undifferentiated colony, the undefined colony, and the differentiated colony are identified based on a luminance B of the colony in the taken image, in addition to the circularity.

The identification of the colonies by means of the luminance is based on the scientific discoveries, in which the undifferentiated multipotent stem cells look dark in the taken image, the differentiated multipotent stem cells look bright in the taken image, and further, the multi-layered multipotent stem cells containing multipotent stem cells that are stacked to form multiple layers look further darker than the undifferentiated multipotent stem cells.

More specifically, it may be configured such that when the undifferentiated colony that is identified based on the circularity C is (A), the undefined colony that is identified based on the circularity C is (B), the differentiated colony that is identified based on the circularity C is (C), a first predetermined threshold for the luminance of the colony is B1, a second predetermined threshold for the luminance of the colony is B2, a third predetermined threshold for the luminance of the colony is B3, and a fourth predetermined threshold for the luminance of the colony is B4 (B1<B2<B3<B4), a colony satisfying B2≤B≤B3 for all luminances within a colony contour is determined as an undifferentiated colony (a), a colony satisfying B<B1 for some of the luminances within the colony contour is determined as a multi-layered colony (d), a colony satisfying B4<B for some of the luminances within the colony contour is determined as a differentiated colony (c), and a colony other than the undifferentiated colony (a), the multi-layered colony (d) and the differentiated colony (c) is determined as an undefined colony (b), then a colony satisfying (A) and (a) is determined as the undifferentiated colony, a colony satisfying (A) and (b), or satisfying (B) and (a), or satisfying (B) and (b) is determined as the undefined colony, a colony satisfying (d) is determined as the multi-layered colony containing multipotent stem cells that are stacked to form multiple layers, and a colony satisfying (c) or (C), and (a) or (C), and (b) is determined as the differentiated colony.

Further, the method for identifying colony according to the present invention may be configured such that a fine image for the undefined colony is further acquired, and the undefiled colony is identified as the undifferentiated colony when a cell within the undefined colony in the fine image is smaller than a predetermined size.

Such identification by means of the size of the cell contained in the undefined colony is based on the discoveries, in which the undifferentiated multipotent stem cell is small, and the differentiated multipotent stem cell is larger than the undifferentiated multipotent stem cell.

In the method for identifying the colony according to the present invention, the aforementioned taken image may preferably be subjected to an image processing to accentuate a contour.

A method for automatically culturing multipotent stein cells, of the present invention, comprises a step for identifying the undifferentiated colony and a colony other than the undifferentiated colony by the above described method for identifying a colony; a step for acquiring positional information of the undifferentiated colony and the colony other than the undifferentiated colony; a step for supplying a cell dissociation agent in the cultivation container; a step for dissociating the undifferentiated colony based on the positional information; and a step for recovering the undifferentiated colony obtained by the dissociation of the undifferentiated colony.

Alternatively, a method for automatically culturing multipotent stem cells, of the present invention comprises a step for identifying a colony other than the undifferentiated colony by the above described method for identifying a colony; a step for acquiring positional information of the colony other than the undifferentiated colony; a step for supplying a cell dissociation agent in the cultivation container; a step for dissociating the colony other than the undifferentiated colony based on the positional information; a step for removing the multipotent stems cell obtained by the dissociation of the colony other than the undifferentiated colony; and a step for dissociating the undifferentiated colony to recover the undifferentiated colony multipotent stem cells.

Alternatively, a method for automatically culturing multipotent stem cells, of the present invention, comprises: a step for identifying the undifferentiated colony by the above described method for identifying a colony; a step for acquiring the number of the undifferentiated colonies and the number of colonies other than the undifferentiated colonies; and a step for dissociating and recovering all colonies by supplying a cell dissociation agent in the cultivation container, when a relation: (number of undifferentiated colonies)/(total number of colonies)≥(predetermined threshold) is satisfied.

In addition, the above-described method may further comprises: a step for further acquiring a fine image for each of the undefined colonies and adding the number of colonies that are determined as the undifferentiated colonies based on the fine image to the number of the undifferentiated colonies to obtain new number of the undifferentiated colonies, when a relation: (number of undifferentiated colonies)/(total number of colonies)<(predetermined threshold) is satisfied; a step for supplying a cell dissociation agent to the cultivation container to dissociate and recover all colonies, when a relation: (new number of undifferentiated colonies)/(total number of colonies)≥(predetermined threshold) is satisfied, and a step for selectively dissociating and recovering the undifferentiated colonies and the undefined colonies determined as the undifferentiated colonies based on the fine image, when a relation: (new number of undifferentiated colonies)/(total number of colonies)<(predetermined threshold) is satisfied.

A device for identifying colonies of the present invention, comprises an image acquisition means for acquiring a taken image inside of an incubator of multipotent stem cells; and an identification means for identifying an differentiated colony and an undifferentiated colony based on a circularity C of the colony obtained from the taken image, wherein, when a predetermined first threshold of the circularity of the colony is C1, and a second predetermined threshold of the circularity of the colony is C2 (C1<C2), the identification means determines that: a colony satisfying C2≤C is the undifferentiated colony containing only undifferentiated multipotent stem cells, a colony satisfying C1≤C<C2 is the undefined colony that is potentially an undifferentiated colony, and a colony satisfying C<C1 is the differentiated colony containing multipotent stem cells.

In addition, the above-described device for identifying colonies may be configured to identify the undifferentiated colony, the undefined colony, and the undefined colony based on a luminance B of the colony in the taken image, in addition to the circularity.

More specifically, this may be configured such that, when the undifferentiated colony that is identified based on the circularity C is (A), the undefined colony that is identified based on the circularity C is (B), the differentiated colony that is identified based on the circularity C is (C), a first predetermined threshold for the luminance of the colony is B1, a second predetermined threshold for the luminance of the colony is B2, a third predetermined threshold for the luminance of the colony is B3, and a fourth predetermined threshold for the luminance of the colony is B4 (B1<B2<B3<B4), the identification means determines a colony satisfying B2≤B≤B3 for all luminances within a colony contour as an undifferentiated colony (a), a colony satisfying B<B1 for some of the luminances within the colony contour as a multi-layered colony (d), a colony satisfying B4<B for some of the luminances within the colony contour as a differentiated colony (c), and a colony other than the undifferentiated colony (a), the multi-layered colony (d) and the differentiated colony (c) as an undefined colony (b), then, the identification means determines that a colony satisfying (A) and (a) is the undifferentiated colony, a colony satisfying (A) and (b), or satisfying (B) and (a), or satisfying (B) and (b) is the undefined colony, a colony satisfying (d) is the multi-layered colony containing multipotent stem cells that are stacked to form multiple layers, and a colony satisfying (c) or (C), and (a) or (C), and (b) is the differentiated colony.

Further, the device for identifying colonies may further comprises: a fine image acquisition means for acquiring a fine image for the undefined colony, the identification means identifies that the undefined colony is the undifferentiated colony when a cell in the undefined colony in the fine image is smaller than a predetermined size.

In the device for identifying colonies according to the present invention, the taken image may preferably be subjected to an image processing to accentuate the contour.

A device for automatically culturing multipotent stem cells of the present invention comprises: the above-described device for identifying colonies; a dissociation agent supply means for supplying a cell dissociation agent in the cultivation container; and a pipetting device for dissociating the undifferentiated colony based on positional information of the respective colonies to recover the undifferentiated colony acquired by the dissociation of the undifferentiated colony.

Alternatively, a device for automatically culturing multipotent stem cells, of the present invention, comprises: the above described device for identifying colonies; a positional information acquisition means for acquiring positional information of a colony other than the undifferentiated colony; a dissociation agent supply means for supplying a cell dissociation agent in the cultivation container; and a pipetting device for dissociating a colony other than the undifferentiated colony based on positional information acquired in the positional information acquisition means, removing the multipotent stem cells acquired by the dissociation of the colony other than the undifferentiated colony, and further dissociating the undifferentiated colony to recover the undifferentiated colony.

Further alternatively, a device for automatically culturing multipotent stem cells of the present invention, comprises: the above described device for identifying colonies; a colony number acquisition means for acquiring the number of the undifferentiated colonies and the number of colonies other than the undifferentiated colonies; and a pipetting device for supplying a cell dissociation agent to the cultivation container to dissociate and recover all colonies, when a relation: (number of undifferentiated colonies)/(total number of colonies)≥(predetermined threshold) is satisfied.

The device for automatically culturing multipotent stem cells may further comprise a fine image acquisition means for further acquiring a fine image for each of the undefined colonies when a relation: (number of undifferentiated colonies)/(total number of colonies)<(predetermined threshold) is satisfied, wherein the colony number acquisition means adds the number of colonies that are determined as the undifferentiated colonies based on the fine image to the number of the undifferentiated colonies to obtain new number of the undifferentiated colonies, and wherein the pipetting device supplies a cell dissociation agent to the cultivation container to dissociate and recover all colonies, when a relation: (new number of undifferentiated colonies)/(total number of colonies)≥(predetermined threshold) is satisfied, and wherein the pipetting device selectively dissociates and recovers the undifferentiated colonies and the undefined colonies determined as the undifferentiated colonies based on the fine image, when a relation: (new number of undifferentiated colonies)/(total number of colonies)<(predetermined threshold) is satisfied.

Advantageous Effects of the Invention

A method and a device for identifying multipotent stem cell colony and a method and a device for automatically culturing multipotent stem cells is configured such that a taken image of the colonies of the multipotent stem cells in the cultivation container is acquired, and the acquired image is subjected to an image processing, and then identifications for the differentiated colony and the undifferentiated colony are made based on the circularity of the respective colonies, so that precise identification on whether the colony is undifferentiated or differentiation can be achieved. Therefore, even if the differentiations of some of the colonies are started on the occasion of the cultivation of the multipotent stem cells, the identifications for only the undifferentiated colonies can also be achieved.

DESCRIPTION OF EMBODIMENTS

Figure 1A:
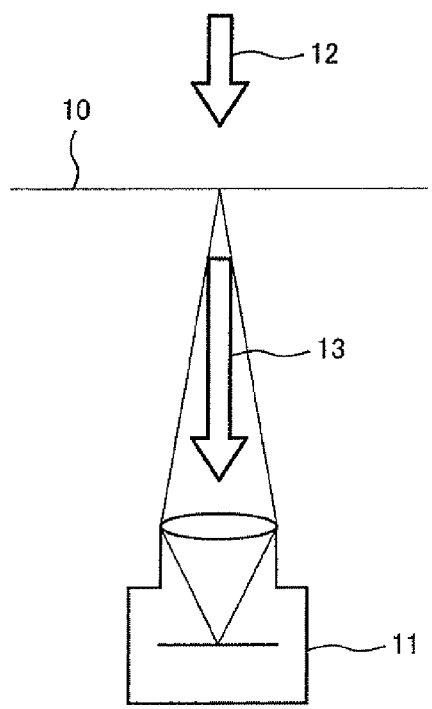
FIG. 1(a) is a schematic diagram, representing a scattering state of illumination light in a dish, which contains no multipotent stem cells.

While the invention will be now described herein with reference to illustrative embodiments, it is not intended that the invention is limited to the descriptions below.

The present invention is made based on a scientific discovery, in which a shape of a colony created only with undifferentiated multipotent stem cells is closer to circular, and a shape of a colony containing differentiated multipotent stem cells is not circular, as described above. In addition to identification whether the colony is a differentiated colony containing differentiated multipotent stem cells or an undifferentiated colony containing only undifferentiated multipotent stem cells, identification for an undefined colony that may be potentially an undifferentiated colony is also automatically conducted by using computers or the like in the method for identifying colony of the present invention. Here, the undefined colony is defined as a colony, which cannot be specified whether the colony is a differentiated colony or an undifferentiated colony, but is potentially an undifferentiated colony. Additionally, identification for a multi-layered colony containing multipotent stem cells that are stacked to form multiple layers can also be conducted, in addition to these identification. For a colony determined as an undefined colony, a fine image is further employed to carry out identification on whether it is a differentiated colony or an undifferentiated colony, as discussed later.

Such identification is conducted by acquiring a wide view image that extensively covers a cultivation container for multipotent stem cells after a cultivation, in which colonies are created, and obtaining circularity and luminance of the respective colonies based on the image after an image processing is made. In addition to above, the image processing of the present invention includes a processing for accentuating a contour of a colony and a processing for normalizing the luminances of the respective pixels to, for example, luminances within a range of monochromatic 0 to 255 gradations (8 bits). Additionally, while the luminance is expressed in 8 bits 256 gradations in the present embodiment, The present invention is not limited thereto, and the steps of the gradations may be increased or decreased.

In the present invention, identification is first conducted based on a shape of a colony. More specifically, the circularity C of the colony: $C=(4\pi S)/(L \times L)$ (S is an area of a colony, and L is a boundary length of a colony) is obtained, and closer to 1 the circularity of the colony is, higher the probability that only the undifferentiated cells are contained in the multipotent stem cells contained in the colony is. While the circularity of the colony is obtained by the formula of $(4\pi S)/(L \times L)$ in the present embodiment, the present invention is not limited thereto, and it may be obtained using other formula if the formula can be used for obtaining the circularity.

In the present invention, related to the circularity C of the colony, the first threshold C1 is defined as a threshold of a boundary between the circularity of the undefined colony that cannot be defined as being either differentiated or undifferentiated and the circularity of the differentiated colony containing the differentiated multipotent stem cells, and the second threshold C2 is defined as a threshold of a boundary between the circularity of the undifferentiated colony containing only the undifferentiated multipotent stem cells and the circularity of the undefined colony (C1<C2). Based on these thresholds, the colony satisfying $C2 \leq C$ is determined as an undifferentiated colony, the colony satisfying $C1 \leq C \leq C2$ is determined as an undefined colony, and the colony satisfying $C<C1$ is determined as a differentiated colony.

Upon acquiring a taken image for employing in the above-described identification of the colony, for example, a Gaussian filter or a median filter is used. The use of these filters allows eliminating noise or images of feeder cells. However, there is still a case, in which identification of a differentiated colony and an undifferentiated colony cannot be precisely conducted only by the circularity, due to the reason, in which an image of larger feeder cells cannot be eliminated by these filters, and the like. In the present embodiment, further precise identification of colonies can be achieved by conducting identification of colonies by means of the luminance in parallel as described below.

Figure 1B:
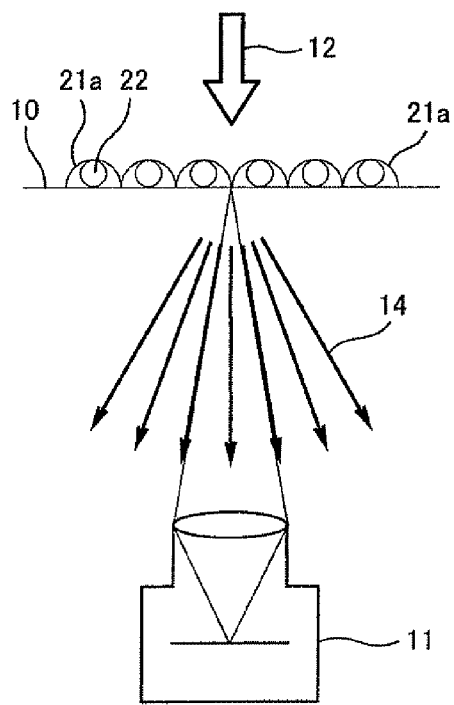
FIG. 1(b) is a schematic diagram, representing a scattering state of illumination light in a dish, which contains multipotent stem cells.
Figure 1C:
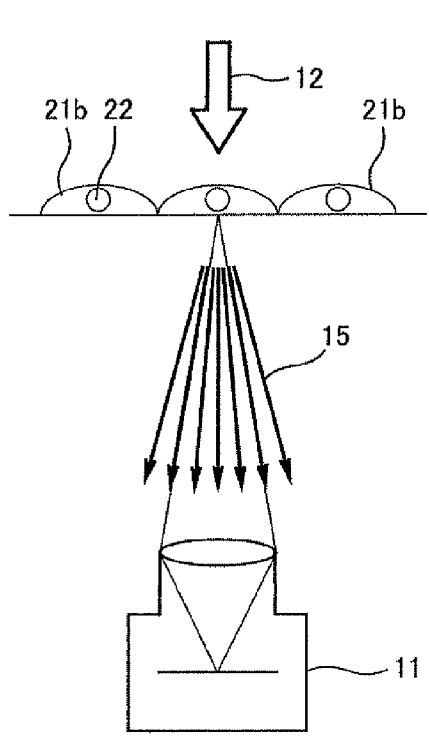
FIG. 1(c) is a schematic diagram, representing a scattering state of illumination light in a dish, which contains differentiated multipotent stem cells.
Figure 1D:
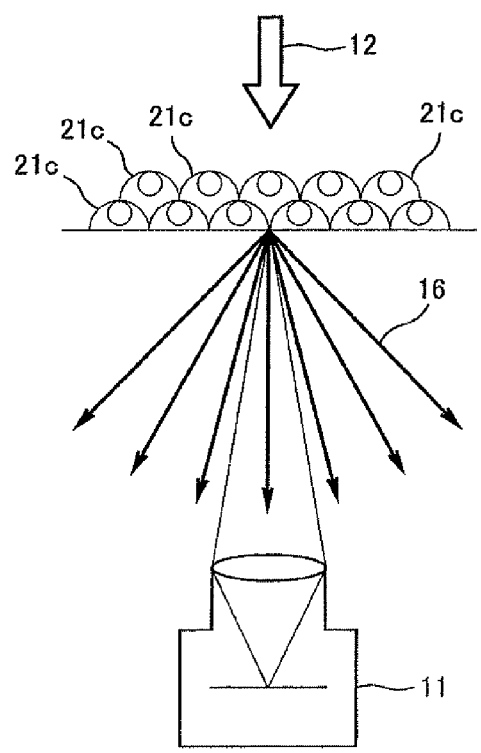
FIG. 1(d) is a schematic diagram, representing a scattering state of illumination light in a dish, which contains multi-layered multipotent stem cells.

The identification of colonies by means of the intensity is based on the following scientific discoveries. More specifically, when no cell or the like is adhered onto a bottom surface 10 of a dish as shown in FIG. 1(a), an illumination light 12 passes through the bottom surface 10 of the dish, and then reaches as an imaging light 13 to an imaging device 11 constituted of a camera and the like without substantially no scattering, and thus the acquired image is brighter. By comparison, when multipotent stem cells or the like is adhered onto the bottom surface 10 of the dish as shown in FIG. 1(b), the illumination light 12 would be scattered by undifferentiated multipotent stem cells 21a. Here, the size of the undifferentiated multipotent stem cell 21a is smaller than the size of the differentiated multipotent stem cell as discussed later, and further, the size of the cell nucleus 22 of cell is not much different between the differentiated cells and the undifferentiated cells, and consequently, the rate of the dimensional area occupied by the portions of a cell other than the cell nucleus 22 is relatively smaller for the undifferentiated multipotent stem cell 21a, as compared with that for the differentiated multipotent stem cell, and thus the illumination light 12 is relatively considerably scattered, as shown in FIG. 1(b). Thus, the imaging light 14 reached to the imaging device 11 is reduced, and the acquired image of the section of the undifferentiated multipotent stem cell 21a is darkened. By comparison, the portion of the cell other than the cell nucleus 22 is relatively larger for the differentiated multipotent stem cell, as shown in FIG. 1(c), and therefore the scattering of the illumination light 12 is reduced, as compared with the case of the undifferentiated multipotent stem cell shown in FIG. 1(b), and an imaging light 15 reached to the imaging device 11 is increased. Therefore, an acquired image of the section of the differentiated multipotent stem cell 21b is brighter than that of the undifferentiated multipotent stem cell of FIG. 1(b). Further, in the case of a multi-layered colony containing multipotent stem cells 21c that are stacked to form multiple layers as shown in FIG. 1(d), which is created by excessive cultivation of multipotent stem cells, the illumination light 12 is more considerably scattered, as compared with the case of FIG. 1(b), so that an imaging light 16 reached to the imaging device 11 is significantly reduced, and an acquired image of the section of the multipotent stem cell 21c is significantly darkened.

In addition to above, when the identification of colony is conducted by means of the strength and weakness of the scattered light as described above, the visibility of cells is different by the lighting method, and therefore it is preferable to emit a transparent illumination light as an illumination light from one direction toward an observing position, so as to be brighter for the differentiated multipotent stem cells, to provide intermediate brightness for the undifferentiated multipotent stem cells, and to provide darker appearance for the multi-layered multipotent stem cells.

Figure 2:
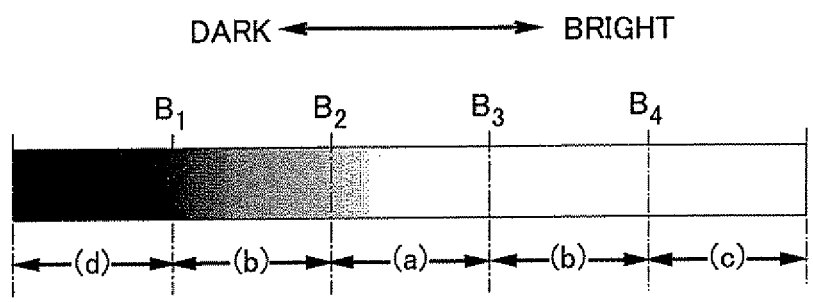
FIG. 2 is a conceptional diagram, representing threshold for identification of colonies in a dish, based on luminance of a taken image.

In the present invention, as shown in FIG. 2, a threshold for the luminance of the taken image is determined. More specifically, the first threshold B1 is determined as a threshold of a boundary between the luminance of the multi-layered multipotent stem cells and the luminance of the undefined multipotent stem cells, the second threshold B2 and the third predetermined threshold B3 are determined as thresholds of a boundary between the luminance of the undefined multipotent stem cells and the luminance of the undifferentiated multipotent stem cells, and the fourth predetermined threshold B4 is determined as a threshold of a boundary between the luminance of the undefined multipotent stem cells and the luminance of the differentiated multipotent stem cells (B1<B2<B3<B4). Upon the identification of the colony based on the luminance B of the multipotent stem cells, the colony satisfying B2≤B≤B3 for all of the luminances within the contour of the colony is determined as the undifferentiated colony, the colony satisfying B<B1 for some of the luminances within the contour of the colony is determined as the multiple-layered colony, and the colony satisfying B4<B for some of the luminances within the contour of the colony is determined as the differentiated colony, the colony other than the undifferentiated colony, the multi-layered colony and differentiated colony is determined as the undefined colony.

In the present invention, a fine image (enlarged image) is further acquired for the undefined colony that cannot be defined as being either differentiated or undifferentiated to eventually make a determination on whether it is the differentiated colony or it is the undifferentiated colony. Here, the fine image is an image, in which a part in the wide view image is represented with an increased size equivalent to that of the wide view image. Since the undifferentiated multipotent stem cell 21*a* (FIG. 1(*b*)) is smaller, as compared with the differentiated multipotent stem cell 21*b* (FIG. 1(*c*)) as described above, the size of the cell is determined by using the fine image to achieve the identification on whether it is the undifferentiated colony or the differentiated colony.

Figure 3:
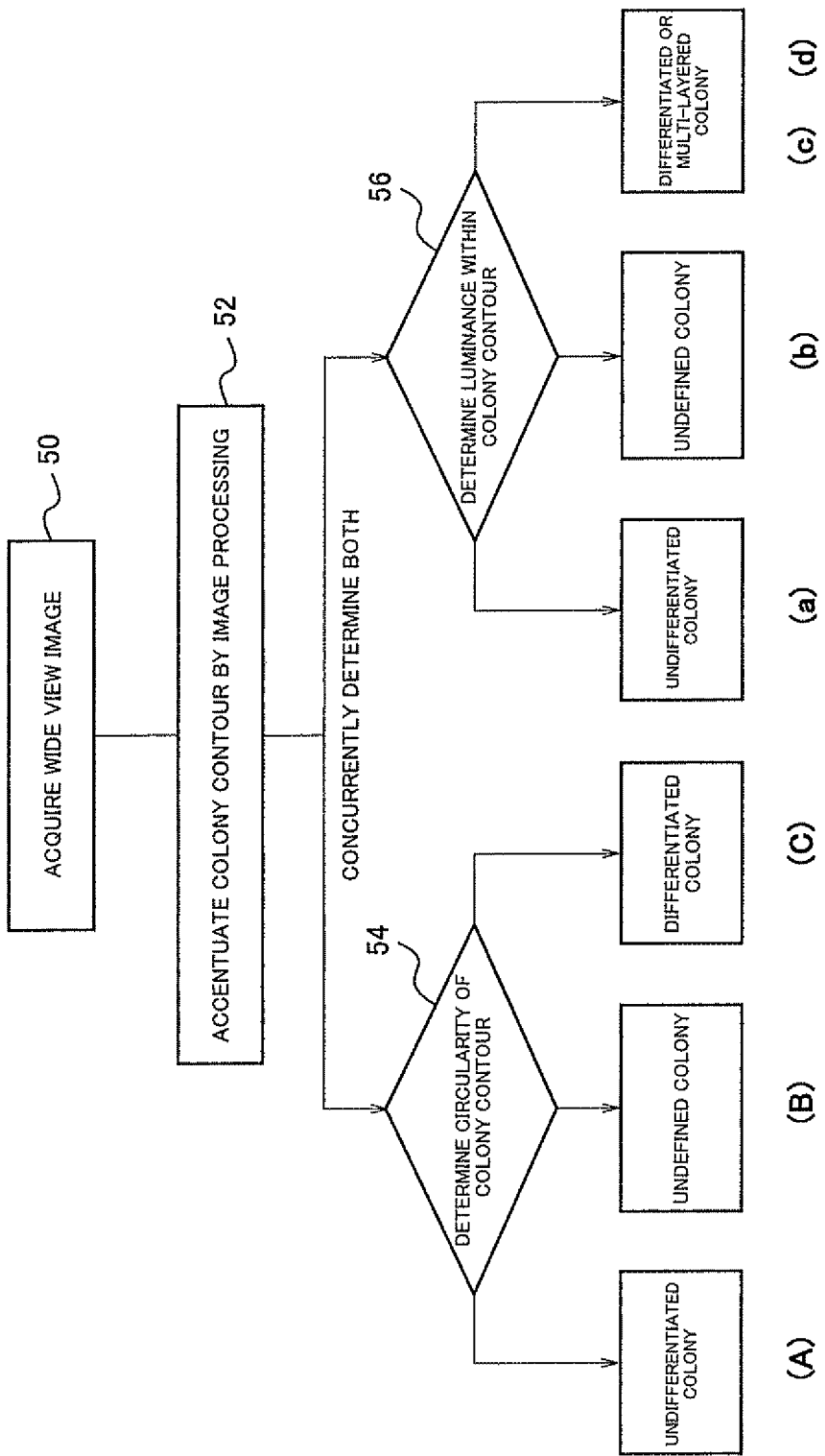
FIG. 3 is a flow chart, representing identification procedure for a colony in an embodiment of the present invention.
Figure 5:
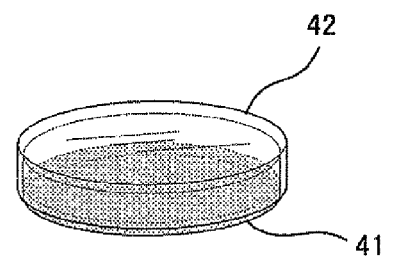
FIG. 5 is a perspective view, representing an imaging device (camera) for acquiring a taken image of the inside of a dish.

FIG. 3 is flow chart, which represents a procedure for the identification of the colony in the embodiment of the present invention. In the present embodiment, first of all, the inside of the dish 41 containing the cultured multipotent stem cells is picked up by a camera 43 through a cover 42 as shown in FIG. 5 to acquire an image of wide view (step 50). This image is image-processed to carry out an accentuated contour, and further to obtain a normalized taken image for luminances of 8 bits (step 52), and this taken image is employed to carry out the above-described identification of the colony and acquisitions of positional information of the respective colonies. Alternatively, the imaging of the inside of the dish 41 may be carried out in the state of removing the cover 42. In the present embodiment, the identification by the circularity C of the colony (step 54 of FIG. 3) and the identification by the luminance B within the contour of the colony (step 56 of FIG. 3) are concurrently conducted. While the identification by the circularity C and the identification by the luminance B are concurrently conducted in the present embodiment, it may be alternatively be configured such that one of these identifications is conducted first, and then the other is conducted. It may be composed of to be conducted the other identification.

In the identification by the circularity C of the colony, as shown in the above-mentioned FIG. 3, the colony satisfying C2≤C is determined as the undifferentiated colony (A), the colony satisfying C1≤C<C2 is determined as the undefined colony (B), and the colony satisfying C<C1 is determined as the differentiated colony (C). Similarly, in the identification based on the luminance B of the multipotent stem cells, as shown in the above-mentioned FIG. 2 and FIG. 3, the colony satisfying B2≤B≤B3 for all luminances within the colony contour is determined as an undifferentiated colony (a), the colony satisfying B<B1 for some of the luminances within the colony contour is determined as a multi-layered colony (d), and the colony satisfying B4<B for some of the luminances within the colony contour is determined as a differentiated colony (c), and the colony other than the undifferentiated colony (a), the multi-layered colony (d) and the differentiated colony (c) is determined as an undefined colony (b).

In the present embodiment, the final identification of the colony is conducted based on the result of the above-described identification by the circularity C of the colony and the result of the above-described identification by the luminance B within the contour of the colony. In the present embodiment, the colony satisfying
(A) and (a)
is determined as the undifferentiated colony, the colony satisfying
(A) and (b), or satisfying (B) and (a), or satisfying (B) and (b)
is determined as the undefined colony, the colony satisfying
(d)
is determined as the multi-layered colony, and the colony satisfying
(c) or (C), and (a) or (C), and (b)
is determined as the differentiated colony.

Figure 4:
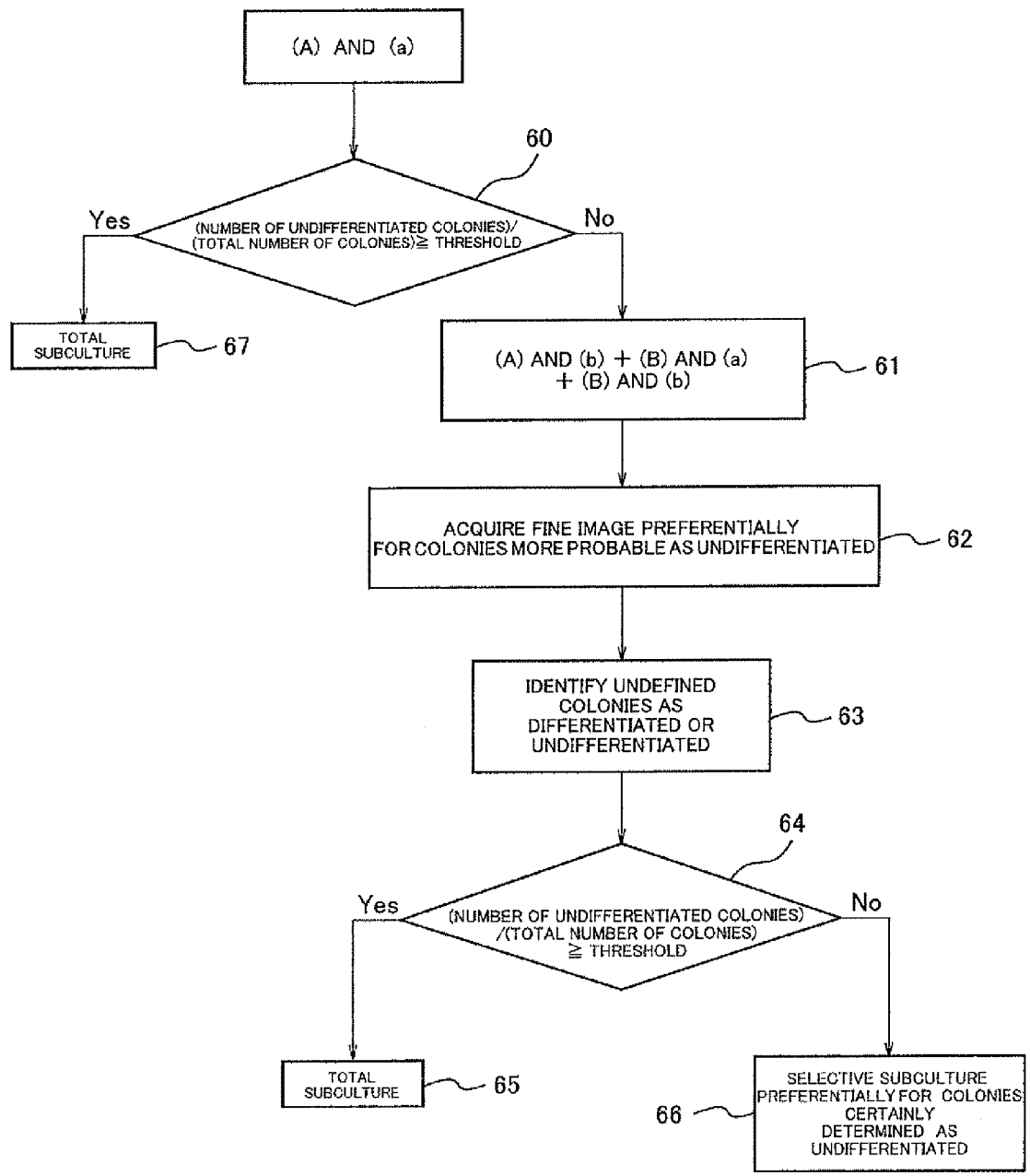
FIG. 4 is a flow chart, representing a treatment conducted after the identification of the colony.

FIG. 4 is a flow chart, which represents the processing after the identification of the colony. In the present embodiment, first of all, a ratio of the number of the undifferentiated colony determined by (A) and (a) over the total number of the colony in the entire cultivation container more specifically, (number of undifferentiated colonies)/(total number of colonies) is obtained (step 60). This ratio is compared with the predetermined threshold, and when it is equal to or larger than the threshold, the dissociation of all colonies in the cultivation container is conducted, and the cells containing both of the undifferentiated and the differentiated multipotent stem cells are totally provided to following subculture (step 67). The dissociation of all colonies in the cultivation container is carried out by supplying the cell dissociation agent in the cultivation container, and then discharging the culture medium from a pipetting device over the entire surface of the cultivation container.

As described above, both of the undifferentiated and the differentiated cells are employed to carry out the total subculture, so that the time required for the screening of the undifferentiated and the differentiated multipotent stem cells can be eliminated, reducing the whole culture time. While such a subculture is accompanied with a subculture of multipotent stem cells which that started the differentiation, properties of such a differentiated multipotent stem cells is different from that of the undifferentiated multipotent stem cells, and therefore the differentiated multipotent stem cells can be easily eliminated by separating the undifferentiated multipotent stem cells in the subculture at the final phase of the cell culture.

By comparison, when the ratio of the above-described (number of undifferentiated colonies)/(total number of colonies) is smaller than the threshold (step 61), fine images (enlarged images) are further acquired for each of the undefined colonies (step 62). In the present embodiment, the image processing similar as employed in the above-mentioned wide view image is also conducted for this fine image. Since it is observed that the undifferentiated multipotent stem cell is smaller and the differentiated multipotent stem cell is larger in the fine image of the colony as described above, it is identified that the undefined colony is the undifferentiated colony when all cells in the fine image is smaller than the predetermined size, and it is identified that the undefined colony is the differentiated colony containing the cells that started the differentiation when larger cells than the predetermined size is contained in the fine image (step 63).

After the identification for either the undifferentiated colony or the differentiated colony is finished for all the undefined colonies as described above, the ratio (number of undifferentiated colonies)/(total number of colonies) is obtained again. Then, this ratio is compared with the predetermined threshold similarly as described above (step 64), and if it is equal to or larger than the threshold, the dissociation of all colonies in the cultivation container is conducted similarly as described above, and the cells containing both of the undifferentiated and the differentiated multipotent stein cells are provided to following subculture. As described above, both of the undifferentiated and the differentiated multipotent stem cells are employed to carry out the next subculture, so that the time required for the screening of the undifferentiated and the differentiated multipotent stem cells can be eliminated, reducing the whole culture time.

Figure 8:
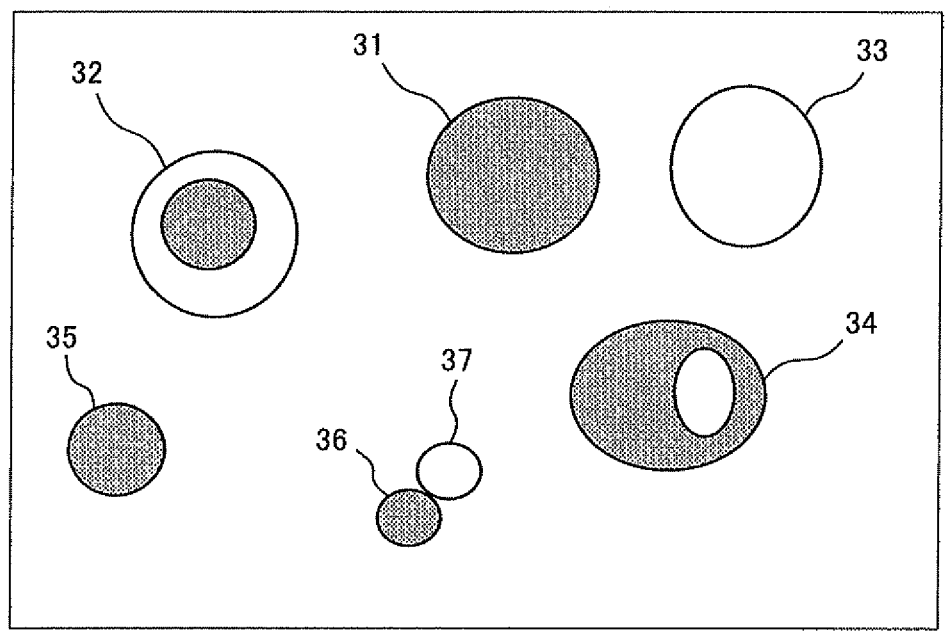
FIG. 8 is a schematic diagram, representing the inside of a cultivation container, in which simultaneously contains differentiation colonies containing differentiated multipotent stem cells and undifferentiated colonies containing only undifferentiated multipotent stem cells.

By comparison, if the above-described ratio (number of undifferentiated colonies)/(total number of colonies) is smaller than the threshold, a selective dissociation for only the undifferentiated colonies is conducted (step 66). FIG. 8 schematically represents a taken image of the cultivation container that contains coexisting undifferentiated colonies and differentiated colonies, and the undifferentiated regions are represented dark, and the differentiated sections are represented with black backgrounds. In FIG. 8, the isolated undifferentiated colonies 31 and 35 composed of only the undifferentiated multipotent stem cells are the colonies that should be recovered by the dissociation. The differentiated colony 32, the peripheral of which started the differentiation, the differentiated colony 33, the whole of which are differentiated, and the differentiated colony 34, the inside of which is partially differentiated are omitted from the colonies that should be separated. By comparison, while the colony 36 is composed of only the undifferentiated multipotent stem cells, when a dissociation is conducted by discharging the solution from the pipetting device as described later, the differentiated multipotent stem cells are dissociated from the differentiated colony 37, which is present in vicinity of the region where the influence of the liquid current of the pipetting can be exerted, such that the undifferentiated colony 36 is not selected. On the occasion of the selection of such an undifferentiated colony, it is necessary to consider that the range for acting the physical force is changed by the type of the chip mounted onto the pipetting device, the discharging rate of the discharging solution and the like. When the dissociation method utilizes a cloning ring, a glass capillary and the like, which provide higher positional accuracy than the pipetting, the dissociation of only the undifferentiated colony can be conducted, even if the distance between the undifferentiated colony and differentiated colony is small.

Figure 6:
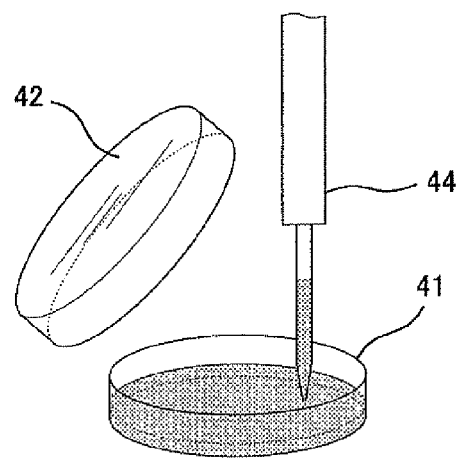
FIG. 6 is a perspective view, representing a pipetting device for conducting a dissociation of an undifferentiated colony by discharging a culture medium via pipetting.
Figure 7:
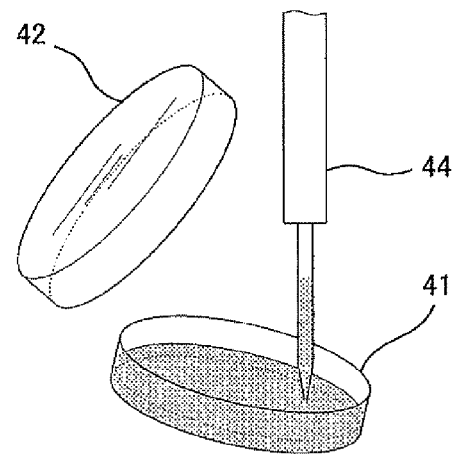
FIG. 7 is a perspective view, representing a pipetting device for conducting a recovery of an undifferentiated colony which is dissociated by pipetting.

Next, after the undifferentiated colony that should have been recovered is selected, a recovery of the undifferentiated colony by pipetting device is conducted. First of all, a cell dissociation agent is introduced to the entire cultivation container. The type, the concentration, the quantity and the like of this dissociation agent is selected, such that cells adhered onto the bottom surface of the dish can be dissociated by the liquid current of the culture medium discharged from the pipetting device during the predetermined time for conducting the dissociation and the cells maintains not to be dissociated from the bottom surface of the dish in the state that there is no liquid current. After the dissociation solution containing the cell dissociation agent is introduced, the culture media is discharged to the selected undifferentiated colonies from the pipetting device 44 as shown in FIG. 6, and thus only the undifferentiated colony is dissociated by this liquid current. The frequency of the discharging of the culture media from the pipetting device is not limited to one, and multiple operations of the discharging may also be made while maintaining the same position or moving, and the discharging rate, the solution amount and the like may also be changed. Once the dissociation of the undifferentiated colonies that should be dissociated is completed, the dish 41 is slanted as required as shown in FIG. 7 to recover the solution that contains the undifferentiated colonies by the pipetting device 44, and when further subculture is required, a part of the solution is also added to the dish 41 that contains new culture media.

Figure 9:
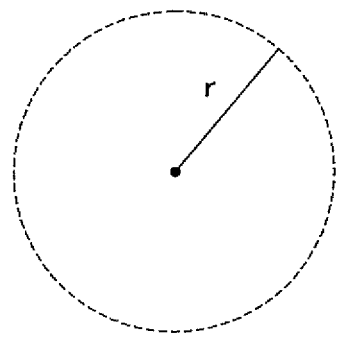
FIG. 9 is a schematic diagram showing range dissociated by a pipetting of once.
Figure 10:
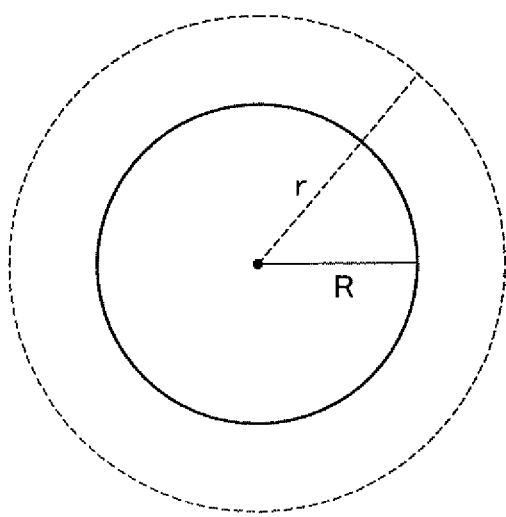
FIG. 10 is a schematic diagram, representing a pipetting operation conducted when a dimension of an undifferentiated colony is smaller than the range dissociated by a single pipetting operation.
Figure 11:
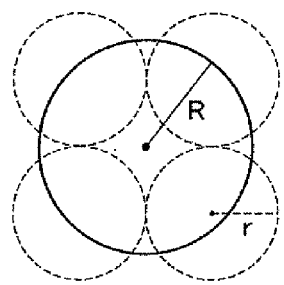
FIG. 11 is a schematic diagram, representing a range of a pipetting conducted when a dimension of an undifferentiated colony is larger than the range dissociated by a single pipetting operation.
Figure 12:
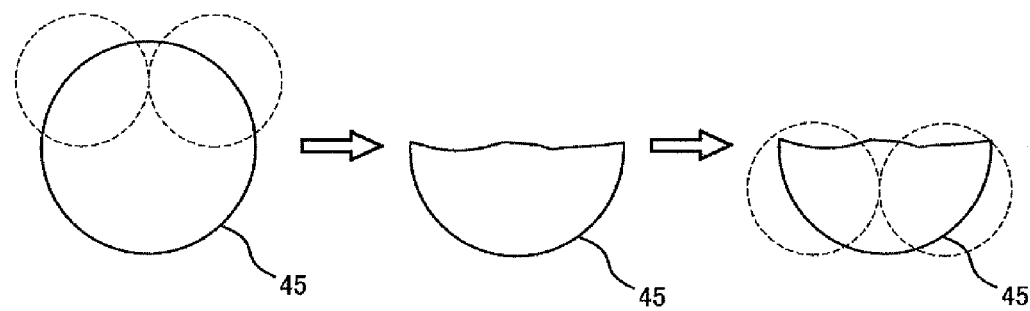
FIG. 12 is a schematic diagram, representing a procedure for a pipetting operation conducted when a dimension of an undifferentiated colony is larger than the range dissociated by a single pipetting operation.
Figure 13:
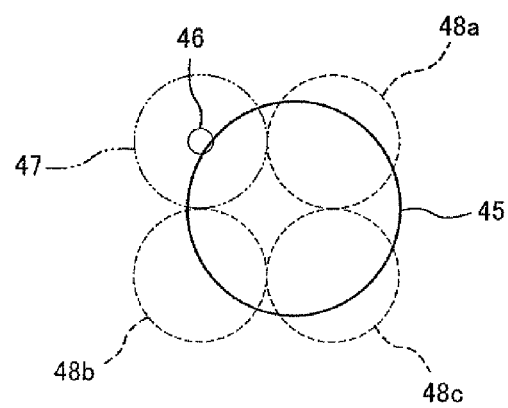
FIG. 13 is a schematic diagram, representing a pipetting operation, when a differentiated colony exists in vicinity of an undifferentiated colony.

Here, the pipetting operation conducted for the dissociation of the undifferentiated colonies will be described. As shown in FIG. 9, the radius of the region where the cells are dissociated by the pipetting is defined as "r". In case of a colony that is in completely isolated situation, in which any other colony to be dissociated such as a differentiated colony is not present in vicinity thereof; when the radius r for being dissociated by the pipetting is larger than a radius R of the undifferentiated colony that should be dissociated as shown in FIG. 10, the whole colony can be dissociated by a single pipetting operation. Additionally, when the radius r of the region where the cells are dissociated by the pipetting is smaller than the radius R of the undifferentiated colony that should be dissociated, the dissociation of the whole undifferentiated colony is conducted by multiple pipetting operations as shown in FIG. 11 (4 operations in FIG. 11). The procedure in that case includes, as shown in FIG. 12, the upper half of the undifferentiated colony 45 is first dissociated by 2 pipetting operations, and once the state is confirmed, further 2 pipetting operations are made to dissociate the lower half of the undifferentiated colony 45 to complete the dissociation of the whole undifferentiated colony. By comparison, when a differentiated colony 46 is present in vicinity of the undifferentiated colony 45 as shown in FIG. 13, no pipetting dissociation is conducted for the region 47 containing the differentiated colony 46, and the pipetting dissociations are conducted for only the three regions, namely the region 48a, the region 48b and the region 48c.

In the present embodiment, a taken image of the colonies of the multipotent stem cells in the cultivation container is acquired, and the acquired image is subjected to an image processing, and then identifications for the differentiated colony and the undifferentiated colony are made based on the circularity and the luminance of the respective colonies, so that precise identification on whether the colony is undifferentiated or differentiation can be achieved. Therefore, even if the differentiations of some of the colonies are started on the occasion of the cultivation of the multipotent stem cells, the identifications for only the undifferentiated colonies can also be achieved. Additionally, when it is found that much of the undifferentiated colonies are contained by the result of the identifications for the colonies in such way, the subcultures are conducted for all colonies in the cultivation container to eventually allow rapid culture of the undifferentiated multipotent stem cells.

While the case of dissociating and recovering only the undifferentiated colony has been described in the above description, it may be alternatively be configured such that all colonies other than the undifferentiated colonies are once dissociated and are removed from the dish by using the pipetting device 44, and then all the undifferentiated colonies remained in the dish are further dissociated and are recovered at one sweep. Alternatively, the recovery of the undifferentiated colonies and the removal of the colonies other than the undifferentiated colonies may be conducted by using different pipetting devices.

INDUSTRIAL APPLICABILITY

According to the method and the device for identifying colony of the multipotent stem cells and according to the method and the device for automatically culturing the multipotent stem cells of the present invention, the undifferentiated multipotent stem cells can be selectively and rapidly subcultured, so that the utilizations in the field of regenerative medicines can be achieved.

REFERENCE CITATION LISTS 10 dish bottom surface
11 imaging device
12 illumination light
13,14,15,16 imaging light
21a undifferentiated multipotent stem cell
21b differentiated multipotent stem cell
21c multipotent stem cells stacked to form multiple layers
22 cell nucleus
41 dish
42 cover
43 camera
31 undifferentiated colony
32,33,34 differentiated colony
35,36 undifferentiated colony
37 differentiated colony
44 pipetting device
45 undifferentiated colony
46 differentiated colony
47 dissociation region
48a, 48b, 48c dissociation region

The invention claimed is:

1. A method for identifying a colony comprising identifying an undifferentiated colony and an undefined colony based on an image taken inside of an incubator of multipotent stem cells, wherein, when a predetermined first threshold of a circularity of the colony is C1 and a second threshold of the circularity of the colony is C2 (C1<C2), a circularity C of the colony obtained from the image is obtained by calculation, and
a colony satisfying
C2≤C
is determined as the undifferentiated colony containing only undifferentiated multipotent stem cells, and
a colony satisfying
C1≤C<C2
is determined as an undefined colony that is potentially the undifferentiated colony.

2. The method for identifying a colony according to claim 1, further comprising determining that a colony satisfying
C<C1
is a differentiated colony containing multipotent stem cells.

3. The method for identifying a colony according to claim 2, wherein the undifferentiated colony, the undefined colony, and the differentiated colony are identified based on a luminance B of the colony in the image, in addition to the circularity.

4. The method for identifying a colony according to claim 3, wherein, when the undifferentiated colony that is identified based on the circularity C is (A), the undefined colony that is identified based on the circularity C is (B), the differentiated colony that is identified based on the circularity C is (C), a first predetermined threshold for the luminance of the colony is B1, a second predetermined threshold for the luminance of the colony is B2, a third predetermined threshold for the luminance of the colony is B3, and a fourth predetermined threshold for the luminance of the colony is B4 (B1<B2<B3<B4), a colony satisfying B2≤B≤B3 for all luminances within a colony contour is determined as an undifferentiated colony (a), a colony satisfying B<B1 for some of the luminances within the colony contour is determined as a multi-layered colony (d), a colony satisfying B4<B for some of the luminances within the colony contour is determined as a differentiated colony (c), and a colony other than the undifferentiated colony (a), the multi-layered colony (d) and the differentiated colony (c) is determined as an undefined colony (b), then
a colony satisfying
(A) and (a)
is determined as the undifferentiated colony,
a colony satisfying
(A) and (b), or satisfying (B) and (a), or satisfying (B) and (b)
is determined as the undefined colony,
a colony satisfying
(d)
is determined as the multi-layered colony containing multipotent stem cells that are stacked to form multiple layers, and
a colony satisfying
(c) or (C), and (a) or (C), and (b)
is determined as the differentiated colony.

5. The method for identifying a colony according to claim 1, further comprising acquiring a fine image for the undefined colony, and identifying the undefined colony as the undifferentiated colony when a cell within the undefined colony in the fine image is smaller than a predetermined size.

6. The method for identifying a colony according to claim 1, wherein the image is subjected to image processing to accentuate a contour of the image.

7. A method for automatically culturing multipotent stem cells, comprising:
for identifying an undifferentiated colony and a colony other than the undifferentiated colony by the method for identifying a colony according to claim 1;
acquiring positional information of the undifferentiated colony and the colony other than the undifferentiated colony;
supplying a cell dissociation agent in the cultivation container;
dissociating the undifferentiated colony based on the positional information; and
recovering the undifferentiated colony obtained by the dissociation of the undifferentiated colony.

8. A method for automatically culturing multipotent stem cells, comprising:
identifying a colony other than an undifferentiated colony by the method for identifying a colony according to claim 1;
acquiring positional information of the colony other than the undifferentiated colony;
supplying a cell dissociation agent in the cultivation container;

dissociating the colony other than the undifferentiated colony based on the positional information;

removing the multipotent stems cell obtained by the dissociation of the colony other than the undifferentiated colony; and dissociating the undifferentiated colony to recover the undifferentiated colony multipotent stem cells.

9. A method for automatically culturing multipotent stem cells, comprising:

identifying an undifferentiated colony by the method for identifying a colony according to claim 1;

acquiring a number of the undifferentiated colonies and the number of colonies other than the undifferentiated colonies; and dissociating and recovering all colonies by supplying a cell dissociation agent in the cultivation container, when a relation:

(number of undifferentiated colonies)/(total number of colonies)≥(predetermined threshold) is satisfied.

10. The method for automatically culturing multipotent stem cells according to claim 9, further comprising:

acquiring a fine image for undefined colonies and adding a number of colonies that are determined as the undifferentiated colonies based on the fine image to the number of the undifferentiated colonies to obtain a new number of the undifferentiated colonies, when a relation:

(number of undifferentiated colonies)/(total number of colonies)<(predetermined threshold)

is satisfied;

supplying a cell dissociation agent to the cultivation container to dissociate and recover all colonies, when a relation:

(new number of undifferentiated colonies)/(total number of colonies)≥(predetermined threshold) is satisfied; and selectively dissociating and recovering the undifferentiated colonies and the undefined colonies determined as the undifferentiated colonies based on the fine image, when a relation:

(new number of undifferentiated colonies)/(total number of colonies)<(predetermined threshold) is satisfied.

11. A device for identifying colonies, comprising:

an image acquisition means for acquiring an image taken inside of an incubator of multipotent stem cells; and an identification means for identifying a differentiated colony and an undifferentiated colony based on a circularity C of the colony obtained from the image, wherein, when a predetermined first threshold of the circularity of the colony is C1, and a second predetermined threshold of the circularity of the colony is C2 (C1<C2), the identification means determines that:

a colony satisfying

C2≤C is the undifferentiated colony containing only undifferentiated multipotent stem cells, a colony satisfying

C1≤C<C2 is an undefined colony that is potentially an undifferentiated colony, and a colony satisfying

C<C1 is the differentiated colony containing multipotent stem cells.

12. The device for identifying colonies according to claim 11, wherein the identification means identifies the undifferentiated colony, the undefined colony, and the undefined colony based on a luminance B of the colony in the image, in addition to the circularity.

13. The device for identifying colonies according to claim 12, wherein when the undifferentiated colony that is identified based on the circularity C is (A), the undefined colony that is identified based on the circularity C is (B), the differentiated colony that is identified based on the circularity C is (C), a first predetermined threshold for the luminance of the colony is B1, a second predetermined threshold for the luminance of the colony is B2, a third predetermined threshold for the luminance of the colony is B3, and a fourth predetermined threshold for the luminance of the colony is B4 (B1<B2<B3<B4), the identification means determines a colony satisfying B2≤B≤B3 for all luminances within a colony contour as an undifferentiated colony (a), a colony satisfying B<B1 for some of the luminances within the colony contour as a multi-layered colony (d), a colony satisfying B4<B for some of the luminances within the colony contour as a differentiated colony (c), and a colony other than the undifferentiated colony (a), the multi-layered colony (d) and the differentiated colony (c) as an undefined colony (b), then, the identification means determines that a colony satisfying (A) and (a)

is the undifferentiated colony, a colony satisfying (A) and (b), or satisfying (B) and (a), or satisfying (B) and (b)

is the undefined colony, a colony satisfying (d)

is the multi-layered colony containing multipotent stem cells that are stacked to form multiple layers, and a colony satisfying (c) or (C), and (a) or (C), and (b)

is the differentiated colony.

14. The device for identifying colonies according to claim 11, further comprising a fine image acquisition means for acquiring a fine image for the undefined colony, the identification means identifies that the undefined colony is the undifferentiated colony when a cell in the undefined colony in the fine image is smaller than a predetermined size.

15. The device for identifying colonies according to claim 11, wherein the image is subjected to image processing to accentuate a contour of the image.

16. A device for automatically culturing multipotent stem cells, comprising:

a device for identifying colonies according to claim 11;

a dissociation agent supply means for supplying cell dissociation agent in the cultivation container; and a pipetting device for dissociating the undifferentiated colony based on positional information of the respective colonies and recovering the undifferentiated colony acquired by the dissociation of the undifferentiated colony.

17. A device for automatically culturing multipotent stem cells, comprising:

a device for identifying colonies according to claim 11;

a positional information acquisition means for acquiring positional information of a colony other than the undifferentiated colony;

a dissociation agent supply means for supplying a cell dissociation agent in the cultivation container; and a pipetting device for dissociating a colony other than the undifferentiated colony based on positional information acquired in the positional information acquisition means, removing the multipotent stem cells acquired by the dissociation of the colony other than the undifferentiated colony, and further dissociating the undifferentiated colony to recover the undifferentiated colony.

18. A device for automatically culturing multipotent stem cells, comprising:
a device for identifying colonies according to claim 11;
a colony number acquisition means for acquiring the number of the undifferentiated colonies and the number of colonies other than the undifferentiated colonies; and
a pipetting device for supplying a cell dissociation agent to the cultivation container to dissociate and recover all colonies, when a relation: (number of undifferentiated colonies)/(total number of colonies)≥(predetermined threshold) is satisfied.

19. The device for automatically culturing multipotent stem cells according to claim 18, further comprising a fine image acquisition means for further acquiring a fine image for each of the undefined colonies when a relation: (number of undifferentiated colonies)/(total number of colonies)<(predetermined threshold) is satisfied, wherein the colony number acquisition means adds the number of colonies that are determined as the undifferentiated colonies based on the fine image to the number of the undifferentiated colonies to obtain new number of the undifferentiated colonies, and wherein the pipetting device supplies a cell dissociation agent to the cultivation container to dissociate and recover all colonies, when a relation:

(new number of undifferentiated colonies)/(total number of colonies)≥(predetermined threshold) is satisfied, and wherein the pipetting device selectively dissociates and recovers the undifferentiated colonies and the undefined colonies determined as the undifferentiated colonies based on the fine image, when a relation:

(new number of undifferentiated colonies)/(total number of colonies)<(predetermined threshold) is satisfied.

* * * * *